US008066676B2

(12) United States Patent
Wilkins

(10) Patent No.: US 8,066,676 B2
(45) Date of Patent: Nov. 29, 2011

(54) CATHETER COMPONENTS FORMED OF POLYMER WITH PARTICLES OR FIBERS

(75) Inventor: Douglas P. Wilkins, San Jose, CA (US)

(73) Assignee: Taylor Medical, Inc., Campbell, CA (US)

( * ) Notice: Subject to any disclaimer, the term of this patent is extended or adjusted under 35 U.S.C. 154(b) by 0 days.

(21) Appl. No.: 11/773,541

(22) Filed: Jul. 5, 2007

(65) Prior Publication Data
US 2008/0027379 A1  Jan. 31, 2008

Related U.S. Application Data

(60) Provisional application No. 60/820,675, filed on Jul. 28, 2006.

(51) Int. Cl.
*A61M 5/178* (2006.01)
*A61M 5/32* (2006.01)
(52) U.S. Cl. ........................ 604/172; 604/265
(58) Field of Classification Search .............. 604/96.01, 604/103.06, 103.09, 103, 164.07, 171, 172, 604/265
See application file for complete search history.

(56) References Cited

U.S. PATENT DOCUMENTS

| | | |
|---|---|---|
| 3,428,046 A | 2/1969 | Remer et al. |
| 3,965,909 A | 6/1976 | Waddell et al. |
| 4,334,037 A | 6/1982 | Allen |
| 4,759,748 A | 7/1988 | Reed |
| 4,762,129 A | 8/1988 | Bonzel |
| 4,955,862 A | 9/1990 | Sepetka |
| 5,040,548 A | 8/1991 | Yock |
| 5,312,356 A | 5/1994 | Engelson et al. |
| 5,554,121 A * | 9/1996 | Ainsworth et al. ........ 604/103.1 |
| 5,851,464 A | 12/1998 | Davila et al. |
| 6,030,360 A | 2/2000 | Biggs |
| 6,086,970 A * | 7/2000 | Ren .............................. 428/36.9 |
| 6,099,499 A * | 8/2000 | Ciamacco, Jr. ............... 604/103 |
| 6,165,158 A | 12/2000 | Dutta |
| 6,379,378 B1 * | 4/2002 | Werneth et al. ............... 607/105 |
| 6,596,020 B2 * | 7/2003 | Vardi et al. .................... 623/1.11 |
| 6,596,818 B1 * | 7/2003 | Zamore ......................... 525/426 |
| 7,163,523 B2 * | 1/2007 | Devens et al. ............. 604/96.01 |
| 2001/0003161 A1 | 6/2001 | Vardi et al. |
| 2003/0229294 A1 | 12/2003 | Bailey et al. |
| 2005/0027248 A1 | 2/2005 | Suzuki et al. |

FOREIGN PATENT DOCUMENTS

| | | |
|---|---|---|
| EP | 1034752 A1 | 9/2000 |
| WO | 9014123 A1 | 11/1990 |
| WO | 9315781 A1 | 8/1993 |
| WO | 9603163 A1 | 2/1996 |
| WO | 9955403 A1 | 11/1999 |

OTHER PUBLICATIONS

Mohs Hardness of Minerals http://www.stone-network.com/rocks/minerals.html.*

* cited by examiner

*Primary Examiner* — Kevin C Sirmons
*Assistant Examiner* — Bradley Osinski
(74) *Attorney, Agent, or Firm* — WRB-IP LLP

(57) ABSTRACT

A guidewire lumen for a catheter includes a tubular member. At least a portion of the tubular member is formed of a compound comprising a polymer and particles or fibers. The particles or fibers can reduce a friction coefficient of the portion of the tubular member while having minimal to no adverse effects with respect to bondability, flexibility, and processability.

57 Claims, 2 Drawing Sheets

CATHETER COMPONENTS FORMED OF POLYMER WITH PARTICLES OR FIBERS

The present application is a non-provisional application of U.S. Provisional Application 60/820,675 filed on Jul. 28, 2006.

BACKGROUND AND SUMMARY

The present invention relates to catheter components and, more particularly, to such components formed of a compound of polymer with particles or fibers.

Cathethers used to treat, e.g., blocked arteries in coronary, peripheral, and neurovascular fields are typically guided to a treatment site by riding over a guidewire. Although the guidewire is sometimes coated with a friction-reducing material such as TEFLON, there is generally some friction when a plastic catheter is pushed over the wire.

In the past, in balloon catheters, polyethylene was used as the balloon material in the catheter. This allowed the use of low friction, High Density Polyethylene (HDPE) as the lumen for the guidewire. A low profile heat bond could be performed at the distal tip of the balloon and the guidewire lumen to allow for a smooth transition and a soft tip.

As more advanced and stronger materials have been developed for the balloon, such as Polyester (PET), Nylon, and Acrylon (Acrylonitrile), a need for an alternative to HDPE has arisen. HDPE as a single material cannot be heat bonded to materials such as Polyester, Nylon, and Acrylon. Some of the materials that can be bonded to Nylon balloons include Polyether Block Amide (PEBAX) and Nylon, however, these materials tend to have higher surface friction than HDPE. One solution has been to coextrude an inner layer of HDPE or TEFLON and an outer layer of some other material, such as PEBAX. This is more costly than an HDPE extrusion, and the coextrusion can result in delamination. Alternatively, an adhesive bond has been used. However, adhesive bonds tend to be undesirably stiff and have a relatively high profile.

Materials with low surface friction such as HDPE, and various fluoropolymers such as PolyTetraFluoroEthylene (PTFE) (also known as TEFLON as manufactured by DuPont), TetraFluorEthylene-Perfluorpropylene (FEP), and PerFluoroAlkoxy (PFA), cannot be heat bonded to many modern balloon materials and are difficult to process. Materials presently used as the guidewire lumen for Nylon balloons are commonly Polyether Block Amide (PEBAX), Nylon 11, Nylon 12, or blends of these materials. Materials used for PET and Acrylon balloons are Hytrel and PET/Polyurethane blends. Polyurethane balloons used for neuro applications also commonly use polyurethane or PEBAX inner wire lumens. All of these materials have high surface frictions at body temperature and have the potential to interfere with guidewire movement.

It is desirable to provide a material suitable for use in a catheter having a low surface friction and that is flexible and easy to process. It is particularly desirable to provide such a material for use in connection with a guidewire lumen.

In accordance with an aspect of the present invention, a guidewire lumen for a catheter comprises a tubular member. At least a portion of the tubular member is formed of a compound comprising a polymer and between about 2-15% particles or fibers by weight.

In accordance with another aspect of the present invention, a catheter comprises a guidewire lumen comprising a tubular member, at least a portion of which tubular member formed of a compound comprising a polymer and particles or fibers. The catheter further comprises a catheter component bonded to the portion of the guidewire lumen without adhesive. A bond strength of a bond between the catheter component and the portion of the guidewire lumen is no more than 10% less than a bond strength of a bond between a second catheter component substantially identical to the catheter component and a portion of a second guidewire lumen substantially identical to the guidewire lumen and formed of the polymer without particles or fibers.

In accordance with yet another aspect of the present invention, a method of making a catheter comprises forming a compound comprising a polymer and between about 2-15% particles or fibers by weight, forming a tubular extrusion of the compound, and bonding the tubular extrusion to a catheter component.

In accordance with yet another aspect of the present invention, a guidewire lumen for a catheter comprises a tubular member. At least a portion of the tubular member is formed of a compound comprising a polymer and particles or fibers. The portion of the tubular member has a coefficient of friction at least 10% lower than a substantially identical tubular member formed of the polymer without the particles or fibers.

In accordance with yet another aspect of the present invention, a tubular catheter component comprises PEBAX compounded with about 2-15% graphite particles, wherein the graphite particles have sizes of about 1-15 μm.

BRIEF DESCRIPTION OF THE DRAWINGS

The features and advantages of the present invention are well understood by reading the following detailed description in conjunction with the drawings in which like numerals indicate similar elements and in which.

DETAILED DESCRIPTION

Figure 1:
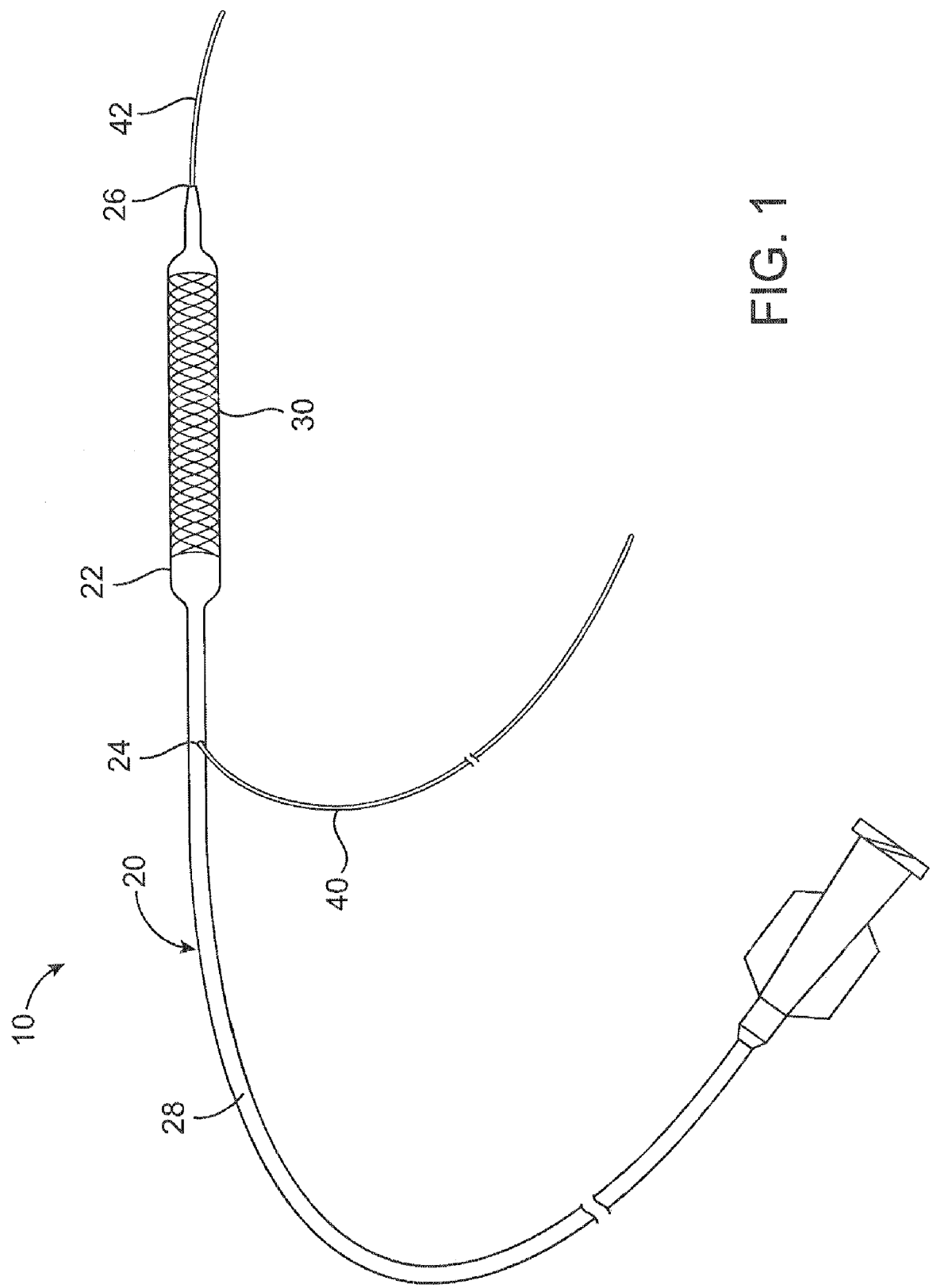
FIG. 1 is a side perspective view of a catheter system.
Figure 2:
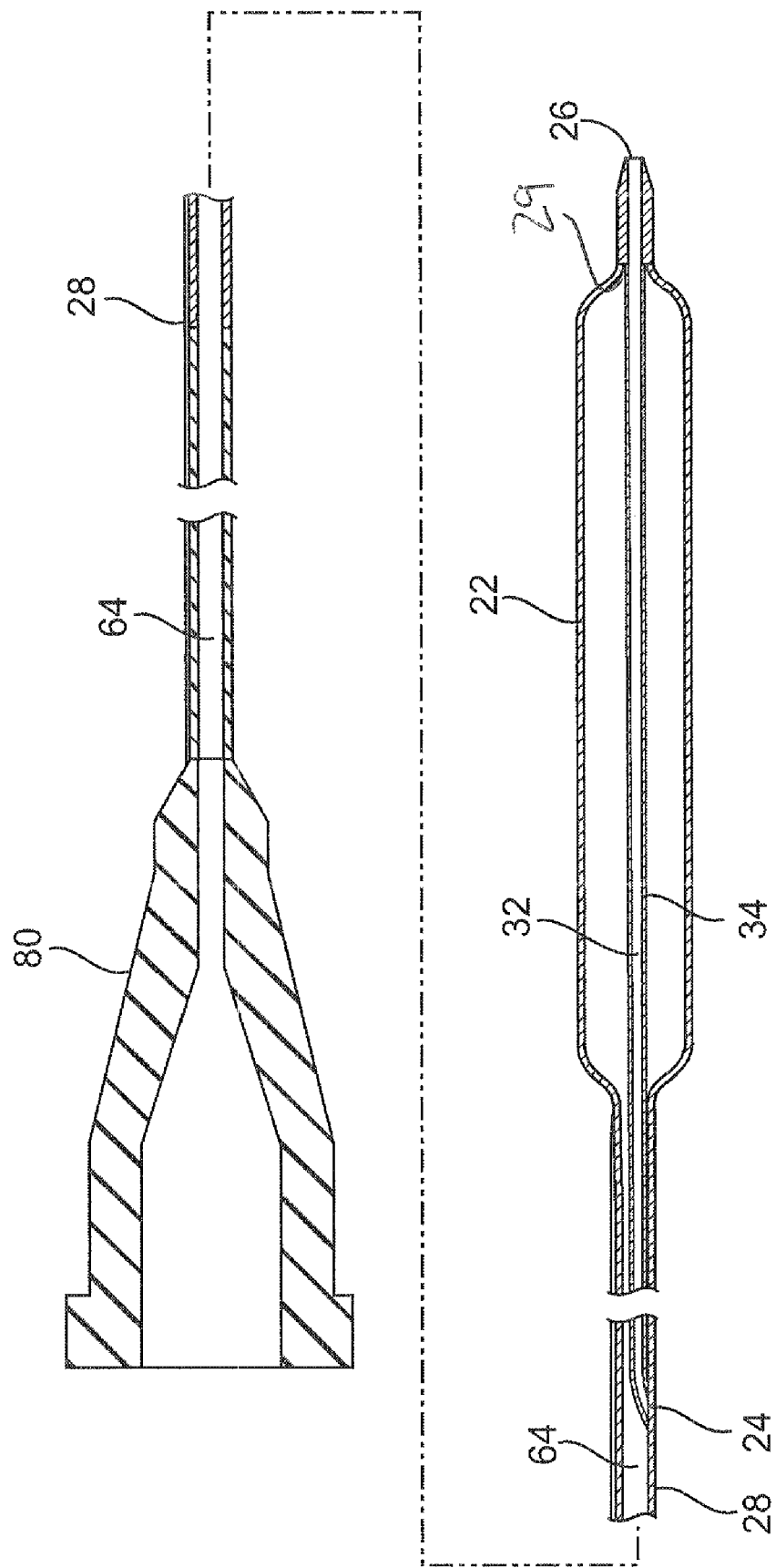
FIG. 2 illustrates a side, elevational, longitudinal cross-sectional view, with central portions broken away, of the catheter illustrated in FIG. 1.

A catheter system 10 comprises a catheter 20 according to an embodiment of the present invention and is shown in FIGS. 1 and 2. The catheter 20 can be a conventional catheter, such as an over-the-wire type catheter or, as shown, a rapid exchange type catheter. The catheter 20 comprises a guidewire lumen 32 through which a guidewire can extend. A proximal portion 40 of the guidewire can extend out of the catheter through a proximal guidewire port 24, or rapid exchange or RX port, that is proximal of a balloon 22, and a distal portion 42 of the guidewire can extend out of a distal guidewire port 26 distal of the balloon 22. The guidewire lumen 32 comprises a tubular member 34 (also referred to as a guidewire lumen or inner member) having an inner opening through which the guidewire 40 can extend. A catheter shaft 28 extends between a hub structure 80 at or proximate a proximal end of the catheter shaft and the balloon 22 at or proximate a distal end of the shaft. The catheter shaft 28 defines an inflation lumen 64. The balloon 22 may be used for angioplasty to expand a stent 30 or for other purposes.

A diameter of the tubular member 34 varies from an outside diameter of about 0.013-0.040 inches (0.33-1.02 mm), and an inside diameter of about 0.010-0.035 inches (0.25-0.89 mm), depending upon the type of catheter. In coronary catheters, the inner tubular member 34 of the guidewire lumen 32 ordinarily has an outside diameter of about 0.019-0.022 inches (0.48-0.56 mm), and an inside diameter of about 0016-0.018 inches (0.41-0.46 mm). For neurocatheters, the outside diameter is typically about 0.013-0.015 inches (0.33-0.38 mm) and the inside diameter is typically about 0.010-0.012 inches (0.25-0.30 mm). In peripheral vascular catheters, an inside diameter is typically about 0.018-0.021 inches (0.46-0.53 mm) and an outside diameter is typically about 0.023-0.026 inches (0.58-0.66 mm). In biliary catheters, an inside diameter is typically about 0.033-0.036 inches (0.84-0.91 mm) and an outside diameter is typically about 0.036-0.039 inches (0.91-0.99 mm).

At least a portion of the tubular member 34 of the guidewire lumen 32, generally substantially the entire tubular member, is formed of a compound comprising a polymer and between about 2-15% particles or fibers by weight, more typically between about 2-10% particles or fibers, and still more typically between about 4-5% particles or fibers. The particles or fibers can be between 1-15 μm in size, and more typically are between 1-μm in size. An average size of the particles or fibers can be about 5 μm. The particles or fibers ordinarily comprise at least one of graphite, barium, bismuth, carbon black, silica, all generally in particle form, and fluoropolymer, such as TEFLON, usually in fiber form. The polymer ordinarily comprises one or more of a polyamide, a nylon, a PEBAX, and polyurethane. The material for coronary catheters is typically PEBAX 72D or 70D or materials of similar hardness. Larger catheters can use these inner lumen materials or stiffer materials. For neuro applications, the material is typically a softer material such as PEBAX 70D, 63D or 55D.

The polymer-particle or fiber compound portion of the tubular member 34 of the guidewire lumen 32 has a lower coefficient of friction than a substantially identical tubular member formed of the polymer without the particles or fibers. The polymer-particle or fiber compound portion of the tubular member 34 of the guidewire lumen 32 is typically extruded as a single integral layer, however, it can be coextruded with other materials. When forming part of the catheter 20, a catheter component such as a distal end 29 of a balloon 22 and/or a catheter shaft 28 of the catheter can be bonded to the polymer-particle or fiber compound portion of the guidewire lumen by any suitable technique, such as by application of heat and pressure, radio frequency bonding, and/or laser bonding. The bond will ordinarily be formed without use of an adhesive, which tends to make a stiff bond having a high profile. A bond strength of the bond between the catheter component and the polymer-particle or fiber compound portion of the guidewire lumen is no less than a predetermined percentage, such as no more than 10% less, than a bond strength of a bond between a second catheter component substantially identical to the catheter component and a portion of a second guidewire lumen substantially identical to the tubular member 34 of the guidewire lumen 32 and formed of the polymer without particles or fibers.

The polymer-particle or fiber compound portion of the tubular member 34 of the guidewire lumen 32 can also have a lower coefficient of friction than a substantially identical tubular member formed of the polymer without the particles or fibers. The coefficient of friction of the polymer-particle or fiber compound portion of the tubular member 34 of the guidewire lumen 32 can be at least 10% lower than the coefficient of friction of the portion of the substantially identical tubular member.

The bond strength may be measured in any suitable fashion. One technique for measuring the bond strength of a bond between the distal end 29 of the balloon 22 and the polymer-particle or fiber compound portion of the tubular member 34 of the guidewire lumen 32 essentially involves separating the bonded part of the balloon and the polymer-particle or fiber compound portion of the tubular member of the guidewire lumen from the rest of the catheter, turning the balloon inside out, and pulling on the balloon and guidewire lumen. Bond strength between the catheter shaft 28 and a polymer-particle or fiber compound portion of the tubular member 34 of the guidewire lumen 32, such as occurs at the "rapid-exchange" (RX) opening, i.e., proximal guidewire port 24, of the catheter shaft is also important and can be measured by, for example, pulling the catheter shaft and the guidewire lumen apart.

Bonds between a distal end of a balloon made of VESTAMID L2124 and various guidewire lumen portions made of several different materials were tested. In addition, bonds at the RX openings of catheter shafts between the catheter shafts and guidewire lumen portions of the several different materials were tested. The results of these tests are shown in Table 1:

| Lumen Type | Sample No. | Lumen-Balloon Bond Strength (lbs) | Lumen-RX Opening Bond Strength (lbs) |
|---|---|---|---|
| Standard Nylon | 1 | 1.47 | 3.12 |
| Standard Nylon | 2 | 1.63 | 2.96 |
| Standard Nylon | 3 | 1.72 | 3.07 |
| PEBAX 72D Hardness with 20% BaSO$_4$ | 1 | 1.91 | 3.01 |
| PEBAX 72D Hardness with 20% BaSO$_4$ Load | 2 | 1.68 | 3.09 |
| PEBAX 72D Hardness with 20% BaSO$_4$ Load | 3 | 1.74 | 2.99 |
| PEBAX 72D Hardness with 5% Graphite Load | 1 | 1.87 | 3.11 |
| PEBAX 72D Hardness with 5% Graphite Load | 2 | 1.90 | 3.07 |
| PEBAX 72D Hardness with 5% Graphite Load | 3 | 1.88 | 3.21 |
| PEBAX 72D Hardness with 5% Carbon Black/Silica Load | 1 | 1.99 | 3.00 |
| PEBAX 72D Hardness with 5% Carbon Black/Silica Load | 2 | 2.01 | 3.01 |
| PEBAX 72D Hardness with 5% Carbon Black/Silica Load | 3 | 1.96 | 3.04 |

In addition, lumens of the type tested in Table 1 were also tested for tendency to collapse at high pressures, which is a measure of how flexible yet strong the lumens are. These are important characteristics with respect to the ease with which a guidewire can be pushed through the lumen while the balloon is inflated. It was considered that there was somewhat greater restriction in certain of the standard nylon and carbon loaded lumens than in the BaSO$_4$ loaded or graphite loaded lumens.

Burst tests of catheters including lumens of the type tested in Table 1 revealed no deficiencies with respect to bursting of the particle loaded PEBAX lumens versus the standard nylon lumens. Bursting in all tests occurred at the balloon between the balloon tapers indicating strong bonds, except that some carbon black loaded lumens burst at the proximal bond area.

In testing of force required to push a wire through lumens of the type tested in Table 1, the graphite loaded PEBAX lumens required the least force, the BaSO$_4$ loaded PEBAX lumens required the next-to-least force, and the most force was required by the carbon black loaded PEBAX lumens and the standard nylon lumens, which both required about the same force.

In a method of making a catheter 20, a compound is formed comprising a polymer and between 2-15% particles or fibers. The compound can be formed by, for example, compounding or mixing in a double screw extruder. A tubular extrusion is formed of the compound. The tubular extrusion forms at least a portion of a tubular member 34 of the guidewire lumen 32 and is bonded to a catheter component such as by having a distal end of the guidewire lumen bonded to a distal end 29 of a balloon 22. Alternatively, or in addition, the catheter component can comprise a catheter shaft 28.

Although the material described herein is described with respect to an inner tubular member 34 of the guidewire lumen 32 member for a rapid exchange or over the wire catheter, the reduced friction coefficient and good bondability of the material for forming the guidewire lumen is also useful in other catheter applications. For example, the material can be used in over the wire catheter proximal shafts. Over the wire catheters generally include an outer shaft and an inner member. The outer proximal shafts of over the wire catheters are generally formed of polymers such as PEBAX or Nylon, however friction between the proximal shaft and the guide catheter can cause reduced pushability of the catheter. Improvements in pushability have been attempted by "frosting" of the catheter outer surface to reduce friction. According to one embodiment of the present invention a proximal shaft of an over the wire catheter is formed of the particle or fiber filled polymer material described herein to improve the pushability and trackability of the catheter.

According to another embodiment, a guide catheter is formed using the particle or fiber filled polymer material as an inner layer to provide improved friction for a catheter passing through the guide catheter and improved bondability of inner layer to other layers of the catheter. A typical guide catheter construction of the present invention includes a graphite filled PEBAX, Nylon, or polyurethane inner layer surrounded by a braid or other strengthening layer, which is covered by an outer layer of PEBAX or other polymer in multiple durometers which change between the proximal and distal ends. The layers are bonded together and the similar materials of the inner and outer layers provide a bond which holds together without delamination problems which occur in known guide catheters having Teflon inner layers. The guide catheter can be a coronary guide catheter.

In the present application, the use of terms such as "including" is open-ended and is intended to have the same meaning as terms such as "comprising" and not preclude the presence of other structure, material, or acts. Similarly, though the use of terms such as "can" or "may" is intended to be open-ended and to reflect that structure, material, or acts are not necessary, the failure to use such terms is not intended to reflect that structure, material, or acts are essential. To the extent that structure, material, or acts are presently considered to be essential, they are identified as such.

While this invention has been illustrated and described in accordance with a preferred embodiment, it is recognized that variations and changes may be made therein without departing from the invention as set forth in the claims.

What is claimed is:

1. A member defining a guidewire lumen for a catheter, comprising a tubular member, at least a portion of which tubular member being formed of a compound consisting of PEBAX and between about 2-15% of one of particles and fibers and formed by a process consisting of compounding the PEBAX and the one of particles and fibers.

2. The member defining a guidewire lumen as set forth in claim 1, wherein the one of particles and fibers is one of graphite, barium, bismuth, carbon black, silica, and fluoropolymer.

3. The member defining a guidewire lumen as set forth in claim 1, wherein the compound comprises between about 2-10% of one of particles and fibers by weight.

4. The member defining a guidewire lumen as set forth in claim 3, wherein the compound comprises between about 4-5% of one of particles and fibers by weight.

5. The member defining a guidewire lumen as set forth in claim 1, wherein the one of particles and fibers are between 1-15 µM in size.

6. The member defining a guidewire lumen as set forth in claim 5, wherein the one of particles and fibers are between 1-10 µm in size.

7. The member defining a guidewire lumen as set forth in claim 5, wherein an average size of the one of particles and fibers is about 5 µm.

8. The member defining a guidewire lumen as set forth in claim 1, wherein a coefficient of friction between the portion of the tubular member and a guidewire is lower than a coefficient of friction between a substantially identical tubular member formed of PEBAX without the one of particles and fibers and the guidewire.

9. The member defining a guidewire lumen as set forth in claim 8, wherein the coefficient of friction between the portion of the tubular member and the guidewire is at least 10% lower than the coefficient of friction between the portion of the substantially identical tubular member and the guidewire.

10. The member defining a guidewire lumen as set forth in claim 1, wherein the portion of the tubular member is extruded as a single layer tube.

11. The member defining a guidewire lumen as set forth in claim 1, wherein at least an inner portion of the tubular member is formed of the compound.

12. The member defining a guidewire lumen as set forth in claim 1, wherein the compound comprises fibers comprising fluoropolymer.

13. The member defining a guidewire lumen as set forth in claim 1, wherein the compound comprises particles of one of graphite, barium, bismuth, carbon black, and silica.

14. The member defining a guidewire lumen as set forth in claim 1, wherein the compound is formed in a double screw extruder.

15. A catheter comprising:
 a member defining a guidewire lumen comprising a tubular member, at least a portion of which tubular member being formed of a compound consisting of PEBAX and one of particles and fibers and formed by a process consisting of compounding the PEBAX and the one of particles and fibers; and
 a catheter component bonded to the portion of the guidewire lumen without adhesive, and
 wherein a bond strength of a bond between the catheter component and the portion of the member defining the guidewire lumen is no more than 10% less than a bond strength of a bond between a second catheter component substantially identical to the catheter component and a portion of a second member defining a guidewire lumen substantially identical to the member defining the guidewire lumen and formed of PEBAX without one of particles and fibers.

16. The catheter as set forth in claim 15, wherein the catheter component comprises a balloon.

17. The catheter as set forth in claim 15, wherein the catheter component comprises a catheter shaft.

18. The catheter as set forth in claim 17, wherein at least a portion of the catheter shaft is formed of a second compound consisting of a polymer and one of particles and fibers.

19. The catheter as set forth in claim 18, wherein the second compound is formed in a double screw extruder.

20. The catheter as set forth in claim 15, comprising a catheter shaft, at least a portion of the catheter shaft being formed of a second compound consisting of a polymer and one of particles and fibers.

21. The catheter as set forth in claim 20, wherein the second compound is formed in a double screw extruder.

22. The catheter as set forth in claim 15, wherein the compound comprises between about 2-15% of one of particles and fibers by weight.

23. The catheter as set forth in claim 15, wherein the one of particles and fibers is one of graphite, barium, bismuth, carbon black, silica, and fluoropolymer.

24. The catheter as set forth in claim 15, wherein a coefficient of friction between the portion of the member defining the guidewire lumen and a guidewire is lower than a coefficient of friction between the portion of the second member defining the guidewire lumen and the guidewire.

25. The catheter as set forth in claim 24, wherein the coefficient of friction between the portion of the member defining the guidewire lumen and the guidewire is at least 10% lower than the coefficient of friction between the portion of the second member defining the guidewire lumen and the guidewire.

26. The catheter as set forth in claim 15, wherein the portion of the member defining the guidewire lumen is extruded as a single layer tube.

27. The catheter as set forth in claim 15, wherein at least an inner portion of the tubular member is formed of the compound.

28. The catheter as set forth in claim 15, wherein the compound is formed in a double screw extruder.

29. A method of making a catheter, comprising:
forming a compound consisting of PEBAX and between about 2-15% of one of particles and fibers by weight by a process consisting of compounding the PEBAX and the one of particles and fibers,
forming a tubular extrusion of the compound; and
bonding the tubular extrusion to a catheter component.

30. The method as set forth in claim 29, wherein the catheter component comprises a balloon.

31. The method as set forth in claim 30, wherein the catheter component comprises a catheter shaft.

32. The method as set forth in claim 29, wherein the catheter component comprises a catheter shaft.

33. The method as set forth in claim 29, wherein the one of particles and fibers is one of graphite, barium, bismuth, carbon black, silica, and fluoropolymer.

34. The method as set forth in claim 29, wherein tubular extrusion is a single layer extrusion.

35. The method as set forth in claim 29, wherein the one of particles and fibers are between 1-15 μm in size.

36. The method as set forth in claim 29, wherein the one of particles and fibers are between 1-10 μm in size.

37. The method as set forth in claim 29, wherein an average size of the one of particles and fibers is about 5 μm.

38. The method as set forth in claim 29, comprising forming at least an inner portion of the tubular member of the compound.

39. The method as set forth in claim 29, comprising forming the compound such that a coefficient of friction between the tubular extrusion and a guidewire is lower than a coefficient of friction between a substantially identical tubular extrusion formed of PEBAX without the one of particles and fibers and the guidewire.

40. The method as set forth in claim 39, wherein the coefficient of friction between the tubular extrusion and the guidewire is at least 10% lower than the coefficient of friction of the portion between the substantially identical tubular extrusion and the guidewire.

41. The method as set forth in claim 29, comprising forming the compound in a double screw extruder.

42. A member defining a guidewire lumen for a catheter, comprising a tubular member, at least a portion of which tubular member being formed of a compound consisting of PEBAX and one of particles and fibers, the compound being formed by a process consisting of compounding the PEBAX and the one of particles and fibers, wherein a coefficient of friction between the portion of the tubular member and a guidewire is at least 10% lower than a coefficient of friction between a substantially identical tubular member formed of PEBAX without the one of particles and fibers and the guidewire.

43. The member defining a guidewire lumen as set forth in claim 42, wherein the one of particles and fibers is one of graphite, barium, bismuth, carbon black, silica, and fluoropolymer.

44. The member defining a guidewire lumen as set forth in claim 42, wherein the compound comprises between about 2-15% of one of particles and fibers by weight.

45. The member defining a guidewire lumen as set forth in claim 44, wherein the compound comprises between about 2-10% of one of particles and fibers by weight.

46. The member defining a guidewire lumen as set forth in claim 42, wherein the compound comprises between about 4-5% of one of particles and fibers by weight.

47. The member defining a guidewire lumen as set forth in claim 42, wherein the one of particles and fibers are between 1-15 μm in size.

48. The member defining a guidewire lumen as set forth in claim 47, wherein the one of particles and fibers are between 1-10 μm in size.

49. The member defining a guidewire lumen as set forth in claim 47, wherein an average size of the one of particles and fibers is about 5 μm.

50. The member defining a guidewire lumen as set forth in claim 42, wherein at least an inner portion of the tubular member is formed of the compound.

51. The member defining a guidewire lumen as set forth in claim 42, wherein the compound is formed in a double screw extruder.

52. A tubular catheter component consisting of:
PEBAX compounded with about 2-15% graphite particles by a process consisting of compounding the PEBAX and the graphite particles, wherein the graphite particles have sizes of about 1-15 μm.

53. The component as set forth in claim 52, wherein the component defines a guidewire lumen.

54. The component as set forth in claim 52, wherein the component is an inner layer of a coronary guide catheter.

55. The component as set forth in claim 52, wherein the component is an outer layer of a balloon catheter shaft.

56. The component as set forth in claim 52, wherein the component is tubular and at least an inner portion of the tubular component is formed of the PEBAX compounded with about 2-15% graphite particles.

57. The component as set forth in claim 52, wherein the compound is formed in a double screw extruder.

* * * * *